(12) United States Patent
Ferrigolo et al.

(10) Patent No.: US 8,920,349 B2
(45) Date of Patent: Dec. 30, 2014

(54) JOINT FOR AN ORTHOPEDIC BRACE WITH TWO ADJUSTABLE ANGULAR RANGE UPRIGHTS

(75) Inventors: Moreno Ferrigolo, Dossobuono (IT); Alberto Turrini, Castel d'Azzano (IT)

(73) Assignee: F.G.P. S.R.L., Dossobuono (VR) (IT)

( * ) Notice: Subject to any disclaimer, the term of this patent is extended or adjusted under 35 U.S.C. 154(b) by 221 days.

(21) Appl. No.: 13/467,520

(22) Filed: May 9, 2012

(65) Prior Publication Data

US 2012/0302932 A1 Nov. 29, 2012

(30) Foreign Application Priority Data

May 27, 2011 (IT) .............................. VR2011A0121

(51) Int. Cl.
*A61F 5/00* (2006.01)
*A61F 5/01* (2006.01)
(52) U.S. Cl.
CPC ....... *A61F 5/0123* (2013.01); *A61F 2005/0144* (2013.01); *A61F 2005/0165* (2013.01)
USPC .................................. 602/16; 602/23; 602/26
(58) Field of Classification Search
USPC .................................... 602/16, 20, 23, 26, 27
See application file for complete search history.

(56) References Cited

U.S. PATENT DOCUMENTS

| 5,662,596 | A | 9/1997 | Young | |
|---|---|---|---|---|
| 7,320,672 | B2 * | 1/2008 | Turrini et al. | 602/26 |
| 7,887,496 | B2 * | 2/2011 | Kahlmeyer et al. | 602/16 |
| 2004/0127825 | A1 | 7/2004 | Castillo et al. | |
| 2006/0173392 | A1 | 8/2006 | Turrini et al. | |
| 2009/0299244 | A1 | 12/2009 | Chiang et al. | |
| 2011/0034843 | A1 * | 2/2011 | Seligman | 602/16 |

FOREIGN PATENT DOCUMENTS

EP 0761186 A2 3/1997
WO WO 2004/078078 A1 9/2004

OTHER PUBLICATIONS

Italian Search Report for IT VR20110121, dated Dec. 14, 2011, The Hague.

* cited by examiner

*Primary Examiner* — Alireza Nia
*Assistant Examiner* — Keri J Nelson
(74) *Attorney, Agent, or Firm* — Greenberg Traurig, LLP

(57) ABSTRACT

A joint with adjustable angular range for a knee brace or other orthopedic braces with two uprights or rods fitted as auxiliary supports for the joints of the human body. The rods consist of two plates connected with rivets, which represent the four joint points of the articulated four-sided figure between the lower upright and the upper upright. Between the plates and the uprights wedges are inserted shaped to the necessary angular range. There is at least one groove and a lowered area which accommodates two teeth of respective tabs located at the two ends of a spring fixed to the outer plate.

10 Claims, 6 Drawing Sheets

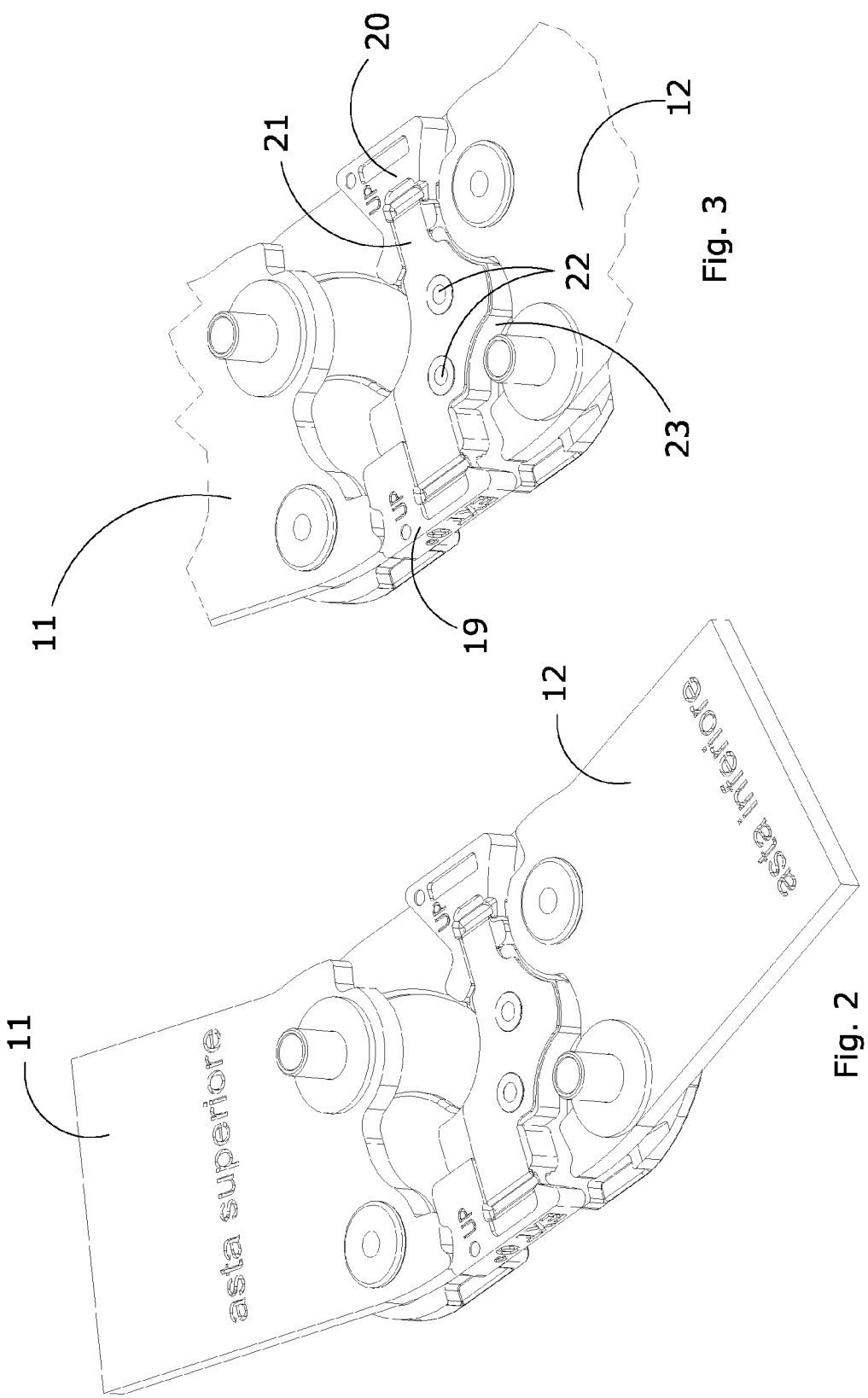

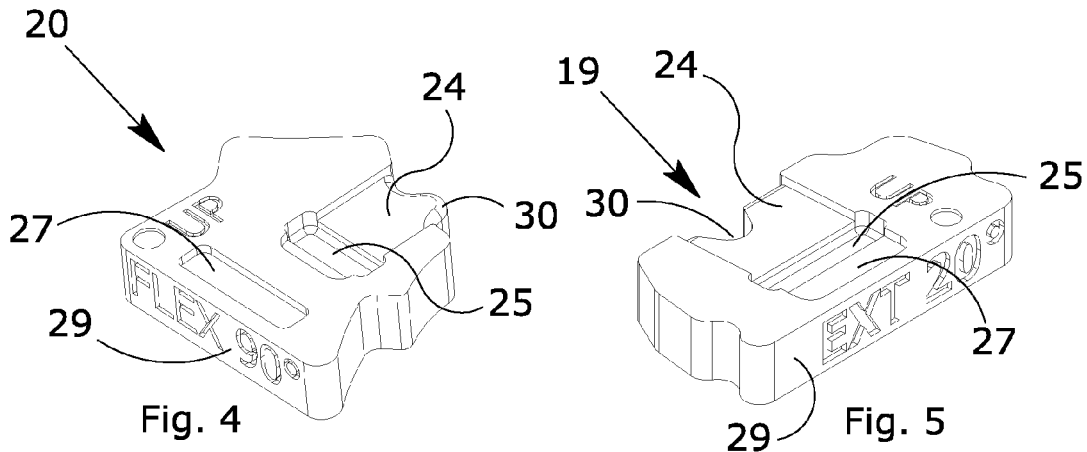
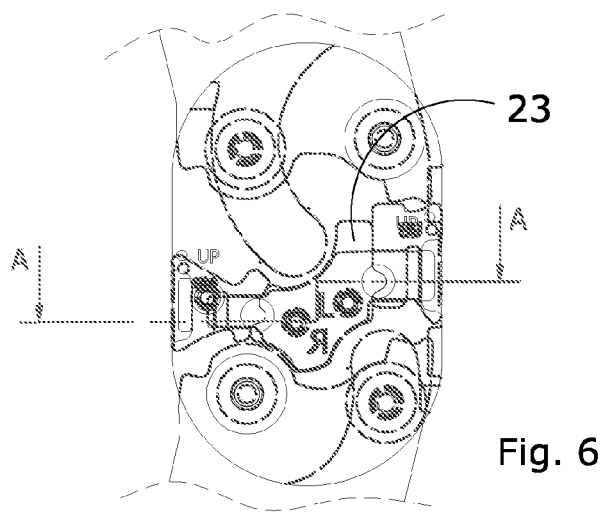
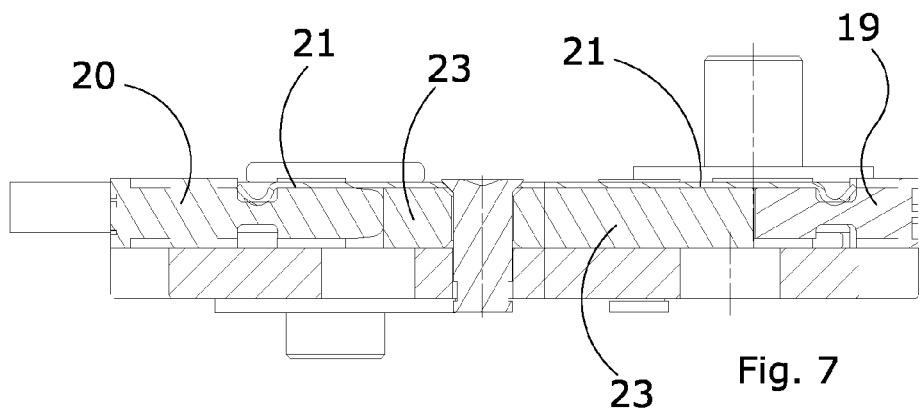

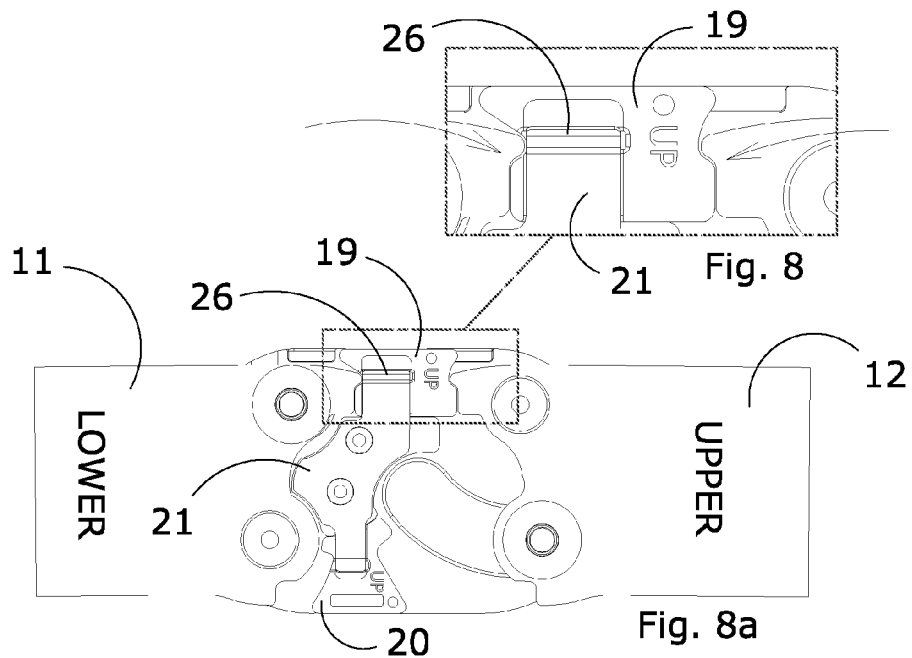
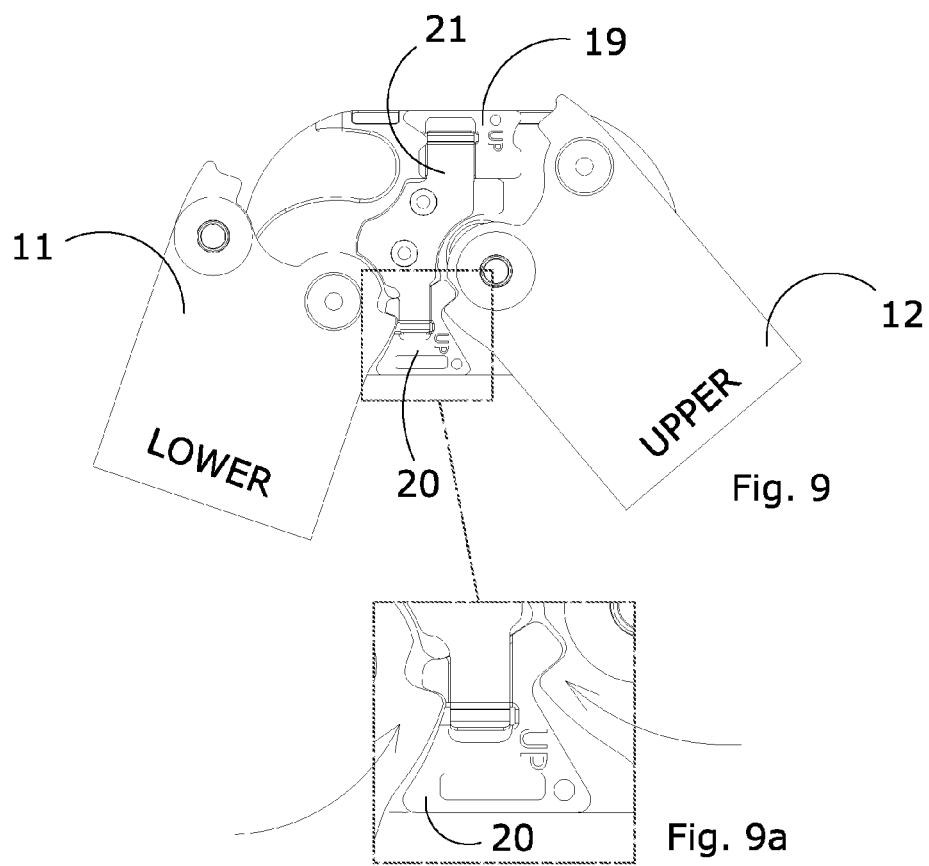

JOINT FOR AN ORTHOPEDIC BRACE WITH TWO ADJUSTABLE ANGULAR RANGE UPRIGHTS

RELATED APPLICATION

This application claims the benefit of and priority to Italian Patent Application Number VR2011A000121, filed May 27, 2011, the contents of which are incorporated by reference herein in its entirety.

BACKGROUND

1. Field

This invention concerns a joint with adjustable angular range for braces, which can be applied as an aid for joints of the human body such as the knee, the ankle, the elbow or similar.

More specifically, this invention refers to a joint for instability control, in particular of the knee, the ankle, the hip or the elbow but in theory for any joint. The joint is therefore part of a knee brace or other similar brace that can be used during sports activities or also during rehabilitation and/or post-operatively.

The joint according to the invention is also used to achieve control of translation, hypertension and rotation of the joint and is equipped with a system of limit stop adjustment to control the angular range both in extension and flexion, in other words it is equipped with a new system of R.O.M. (Range Of Motion) adjustment.

This invention can be applied in the orthopedics industry with particular reference to manufacturers of prostheses and braces.

2. Background Art

It is known that subjects with orthopedic problems of the knee, ankle or elbow joints, above all as the result of a previous surgical operation, need to use an orthopedic brace designed to guarantee the function of a hinged constraint between the femur and the tibia or other joint lever points, supporting stress that would otherwise be harmful for the joint.

It is in fact known that the function of a brace is, in general, to guarantee the relative immobilisation, or limitation, of a joint affected, for example, by trauma, arthrosis, sprained ligaments or which have undergone surgery.

Another use of braces is functional rehabilitation or re-education, where the brace can be used to reduce the load on a joint and lessen the pain, or used for preventive purposes in cases of osteoporosis or bone fragility.

Knee braces usually consist of a rigid and enclosing frame designed to guarantee adequate harnessing of the joint and prevent the onset of strain on the ligaments and synovial membranes when the injured and/or convalescent subject is walking.

According to background art, in the specific case of the knee, the frame of the knee brace comprises means of constraint for the femur and the tibia in areas close to the knee and a structure connecting these means with a jointed hinge positioned at the level of the knee. The means of constraint usually consist of half-rings encircling both the femur and the tibia of the injured subject.

The frame of the knee brace comprises uprights, positioned laterally with respect to the femur and the tibia, connected by respective joints generally equipped with 4 pivots designed to ensure excellent mobility achieved by the presence of multiple centres of rotation.

To ensure adequate freedom of movement of the joint, the frame develops almost exclusively at the sides of the knee in order to allow the correct reciprocal oscillation between the femur and the tibia.

Joints with four pivots are used to ensure the hinged connection of the portions of frame fixed to the femur and to the tibia and they extend during of the joint and shorten when the joint is extended.

This considerably reduces the risk of relative movements of the knee brace and of it slipping downwards.

It is also known that, depending on the severity of the injury, each subject needs different levels of angular range freedom, and braces have thus been produced that comprise means for the adjustable limitation of angular range.

Traditional joints for knee braces with adjustable angular range generally comprise a platform equipped with at least one pair of hinge couplings for the respective uprights, equipped with means for restraining the joint in question, in which said platform comprises a central shaped plate and at least one housing for an extractable insert which abuts against the plate and at least one end of an upright.

The joint comprises means of temporary restraint for the inserts with the purpose of limiting the movement of the joint in extension and/or flexion; in order to be able to adjust the R.O.M. in the various possible angular configurations, the flexion and extension limiting insert must be interchangeable with inserts having different profiles.

The shape of the inserts is such as to limit the reciprocal angular range between the uprights constrained to the joint, the shape differing in order to obtain different angular ranges according to the insert used.

According to the known solutions, the joint presents internal housings for the inserts, consisting of accessible slots formed inside the platform. At the level of each slot, the base surface of the platform presents an opening designed to make the housing of the respective insert visible.

While these solutions solve the problems concerning the R.O.M. (Range of Motion) adjustment system of orthopedic braces with angular range, they show other problems which will be described below.

First of all, the traditional insert system makes use of components of a certain size, creating a first difficulty in the use of the brace due to the considerable thickness of each hinge. The adjustment system is also difficult to use as regards the limited stability of the inserts and it is also difficult to change the inserts when it is necessary to vary the range.

In addition, also according to known solutions, the replacement of the wedge inserts involves the use of specific tools such, for example, screwdrivers to remove the screws and other components fixed on the joint, thus further complicating the replacement steps.

Document WO-A-2004/078078 discloses a joint with adjustable angular range for a knee brace comprising two rods, two plates connected to each other by rivets which represent four joint points, and two wedges insertable between the plates. The wedges are inserted and extracted by means of a specific tool such as a screwdriver.

DESCRIPTION OF THE INVENTION

This invention proposes to provide a joint with adjustable angular range for knee braces or other orthopedic braces, which can be applied as an aid for joints of the human body such as the knee, the ankle, the elbow or similar, that is able to eliminate or at least reduce the drawbacks described above.

The invention also proposes to provide a joint with adjustable angular range for orthopedic braces that presents an innovative system for controlling the relative angle of inclination between two rods connected to it.

This is achieved by means of a joint with adjustable angular range for orthopedic braces, whose features are described in the main claim.

The dependent claims describe advantageous forms of embodiment of the invention.

The main advantages of this solution concern first of all the fact that system for controlling the angular range is, with respect to known solutions, more precise, more simple to use, more compact from an overall dimensions pint of view and therefore more comfortable to wear and use.

In addition, the angular range or R.O.M. adjustment system presents the advantage of insertion and extraction of wedge inserts, also called stops, without the use of specific tools, such as, for example, screwdrivers in the event of the presence of blocking screws.

The adjustable angular range joint for orthopedic braces according to the invention foresees that the fulcrum of the two rods, which form the uprights attached by straps to the legs and made parallel to the femur and tibia, consists of two plates connected to each other by rivets and comprising a spring which has the dual purpose of maintaining the stops in position and prevent them from slipping out.

This spring is fixed to the outer plate by two conical-head rivets which also restrain the central insert, which acts as a rest for the wedge stops, a support for the spring and a limit stop for the rods when the stops are not inserted.

DESCRIPTION OF THE DRAWINGS

Other features and advantages of the invention will become clear on reading the description given below of one embodiment, provided as a non-binding example, with the help of the accompanying drawings, in which:

FIGS. 2 and 3 show schematic prospective views of the joint;

FIGS. 4 and 5 are schematic views showing two possible shapes of the limited range of angular range stop profiles;

FIG. 6 is a front view of the joint;

FIG. 7 is a cross-section view along the lines A-A of FIG. 6;

FIG. 8 shows a view of the joint with reference to a detail of the wedge stop insertion area during extension (front);

FIG. 9 shows a view of the joint with reference to a detail of the wedge stop insertion area during flexion (rear);

DESCRIPTION OF ONE EMBODIMENT OF THE INVENTION

Figure 1:
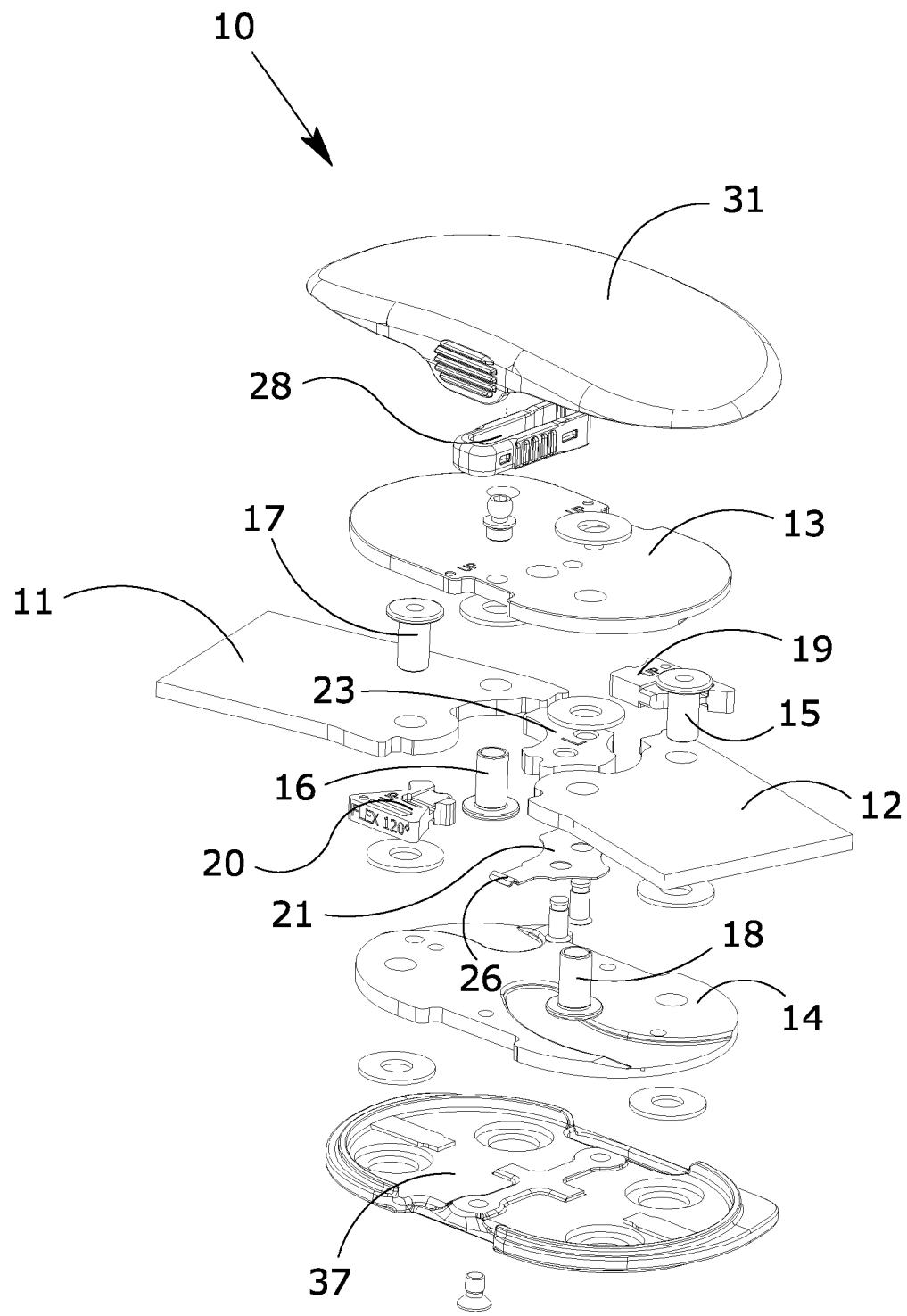
FIG. 1 is an exploded schematic view of the joint according to the invention.

With reference to the accompanying figures, and initially to the exploded view in FIG. 1, the joint device indicated overall with reference number 10 allows the adjustable and controlled angular range between the two uprights or rods 11 and 12, which, in the case of a knee brace, consist respectively of a femoral rod and a tibial rod.

The solution presented is a joint 10 equipped with a system for control of the relative angle of inclination between two rods 11 and 12 connected to it.

The fulcrum of these two rods 11 and 12, which will be attached to the leg by means of straps and made parallel to the femur and the tibia, consists of two plates 13 and 14 connected together by rivets 15 and 16, 17 and 18, which represent the four joint points of the articulated four-sided figure between the tibial upright 11 and the femoral upright 12.

In the case in question of a knee brace, the angle between the two rods will correspond to the angle between the femur and the tibia.

The particular feature of the invention is represented by the ergonomic system of insertion and extraction of a pair of wedges 19 and 20 with which the joint is equipped.

The wedges 19 and 20, the first of which is designed to limit the extension of the brace and the second the flexion, are rigid elements which are interposed wedge-like between the two rods 11 and 12 to limit their movement.

The advantage of the joint system according to the invention is that it allows insertion and extraction of the wedges without the use of specific tools, such as, for example, screwdrivers in the event of the presence of blocking screws.

In the centre, between the two plates 13 and 14, is a spring 21 which is fixed to the outer plate 13 by means of a shaped insert 23 which has the dual purpose of maintaining the wedge in position and preventing it from slipping out.

As can be seen in FIG. 3, the spring 21 is fixed to the outer plate 13 by two conical-head rivets 22 which also restrain the central insert 23, the latter acting as a rest for the wedges, a support for the spring and a limit stop for the rods when the wedges are not inserted.

As can be seen in FIGS. 4 and 5, which show the wedges 19 and 20 in detail, these wedges present a groove 24 which accommodates one of the two tabs positioned at the two ends of the spring, this groove terminating with a lowered area 25 which accommodates one of the two teeth 26 of the spring 21 positioned at the two ends of the two tabs of the spring 21.

Each wedge 19, 20 also comprises an additional lowered area 27 to accommodate a gripper 28 for extraction of each wedge 19, 20. These lowered areas 27 form housings or pockets which are present on both sides of the wedges, in order to make the wedges both left- and right-hand.

The side of each wedge presents wording 29 indicating the angular value it must limit in the R.O.M. function.

On the stop insertion side is a spoked bevel 30 which allows deformation of the spring and its insertion in the groove 24.

As can be seen in FIG. 7, which shows the cross-section of the joint, the function of the spring 21 is to be first inserted in the groove 24 and then in the lowered areas 25 of the wedges 19, 20, which are designed to operate by compression.

In fact, the wedges are interposed between the two rods 11 and 12 to lock them in a certain relative angular position.

Figure 10:
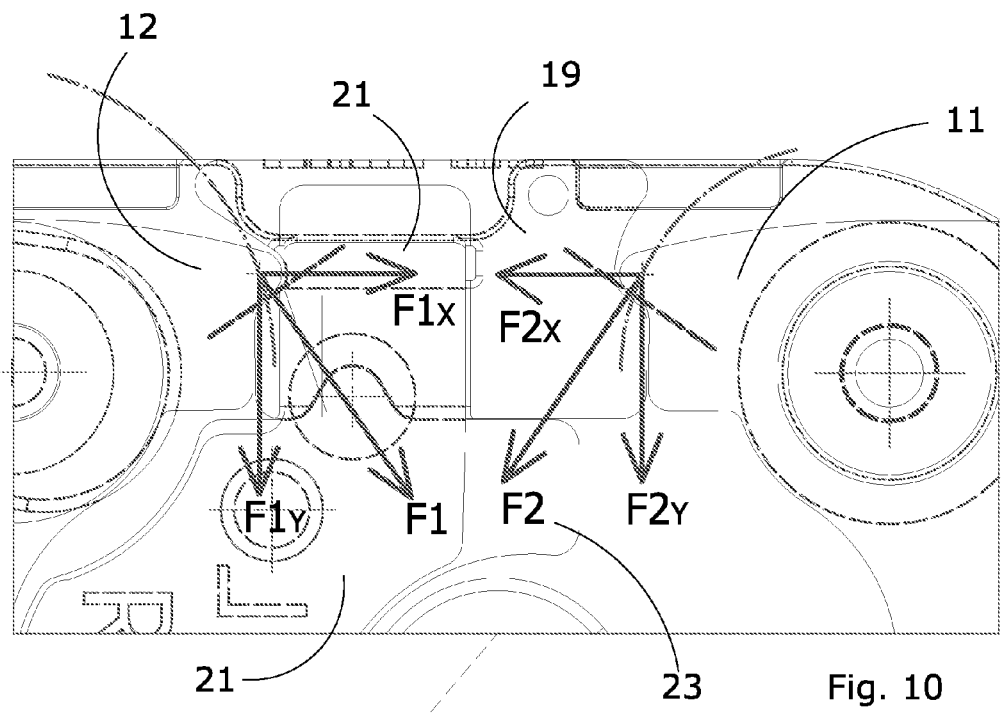
FIG. 10 is a schematic view showing the forces in play in the presence of one of the wedge stops between the joints of the two uprights.
Figure 10A:
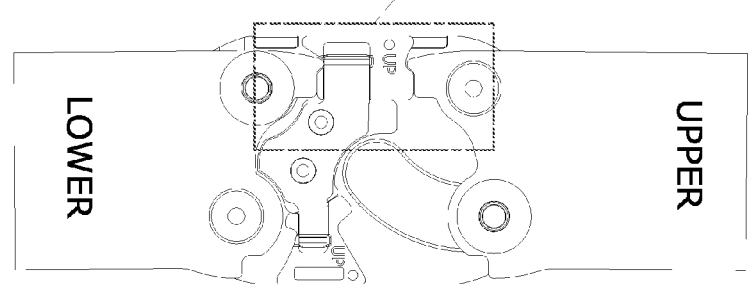

As can be seen in FIG. 10, the shape of the wedges 19, 20 is such that the opposite ends of the rods touch the wedges at the same time, thus preventing any movement and deviation of the wedges.

It can be observed that when the shaped ends of the rods 11 and 12 encounter the wedges 19, 20, they generate a vectorial force which is distributed as shown in FIG. 10, with horizontal opposed components $F1x$ and $F2x$ that cancel each other out.

The vertical components $F1y$ and $F2y$ hold the wedge in position and are directed towards the central insert 23.

In this way, the wedges 19, 20, being inserted between the rods 11 and 12, cannot slip out and the restraining force of the spring 21 allows just the wedges to be held in position when they are not operating.

For additional safety in preventing the accidental slipping out of the wedges, in the most reliable way possible, a protective cap 31 is provided, forming an outer cover of the joint, as can be seen in the exploded view in FIG. 1.

This cap 31, once fixed on the joint, protects the joint, makes its appearance more attractive and ensures that the stops are held in position.

Figure 13:
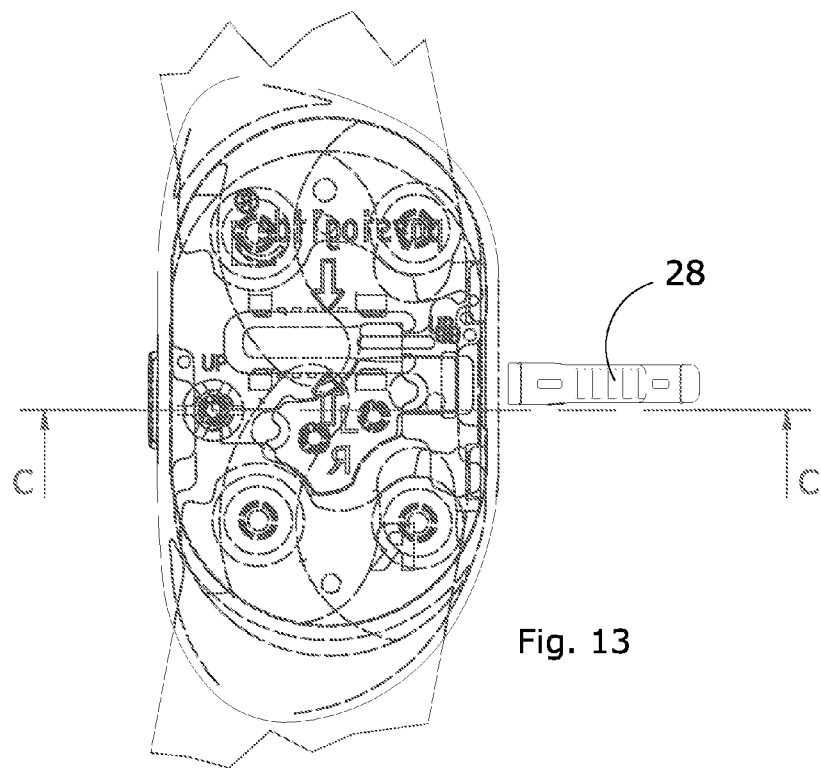
FIG. 13 is a front view of the joint according to the invention.

The conformation of the assembled joint can be seen in FIG. 13. At the point indicated by the arrow 32, the part of the cap 31 that ensures that the wedges are held in place can be seen.

Figure 12A:
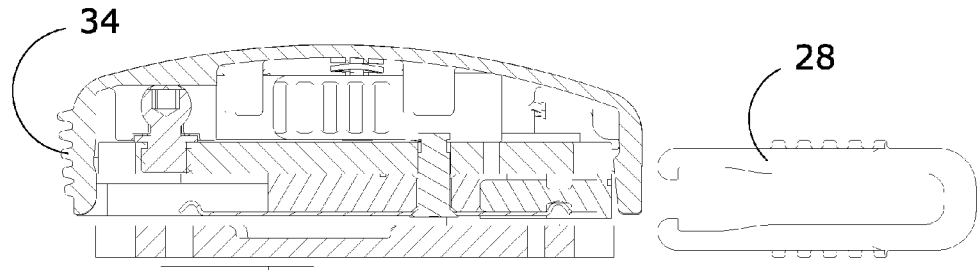
FIG. 12 is a cross-section view along the lines C-C of FIG. 13.
Figure 12:
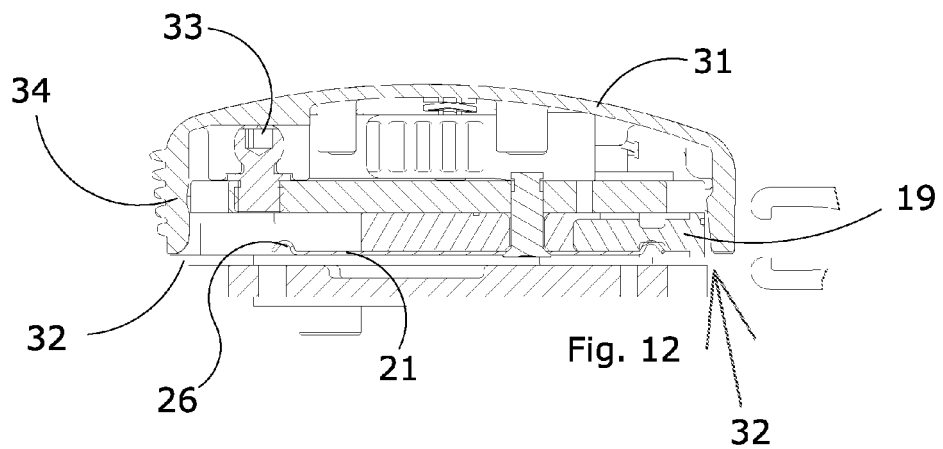

In the cross-section shown in FIG. 12, the left wedge 20 is missing and only the right wedge 19 is present, thus showing the shape of the spring 21 at its end, that is to say the part which holds the wedge in place.

Also in FIG. 12 it can be noted that there is a coupling pin 33 and, on the outer side of the cap 31, toothing 34 making the release of the pin easier.

Inside the cap is a coupling system that allows the positioning and restraint of a gripper 28 to make it available for future use.

Figure 11:
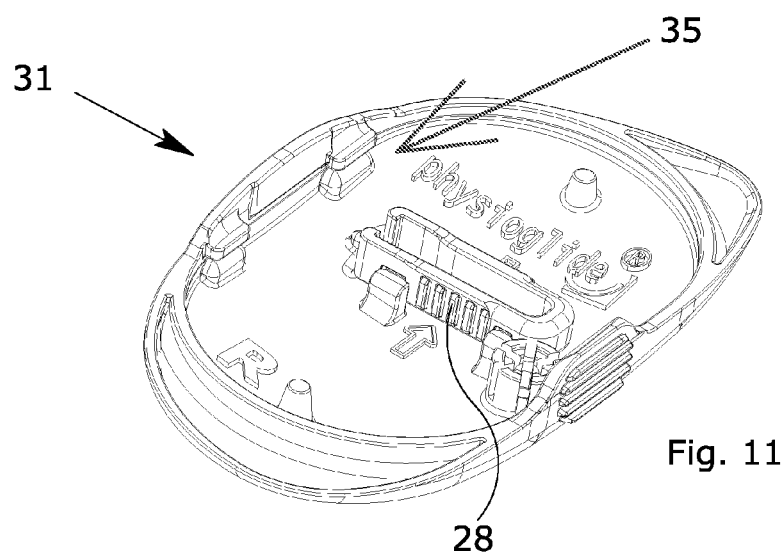
FIG. 11 is a view of the closing cover.

In FIG. 11, the gripper 28 can be seen held in the place when not in use.

The arrow 35 in FIG. 11 shows the coupling teeth of the cap on the outer plate. FIG. 1 shows the closing cap 37 on the inner side of the joint.

As can be noted, the above-mentioned main advantages of this solution have been achieved and concern the fact that system for controlling the angular range is, with respect to known solutions, more precise, more simple to use, more compact from an overall dimensions pint of view and therefore more comfortable to wear and use.

The invention is described above with reference to a preferred embodiment.

The invention claimed is:

1. A joint with adjustable angular range for a knee brace or other orthopedic braces with two uprights or rods having respective shaped ends, which can be fitted as auxiliary supports for the joints of a human body, selectively a knee, an ankle, or an elbow, the two uprights or rods being a lower upright or rod and an upper upright or rod and having between them, the pivot comprising two plates, namely an outer plate and an inner plate, connected to each other at four locations which represent four joint points of an articulated four-sided figure between the lower upright or rod and the upper upright or rod, further comprising wedges to be inserted between said outer and inner plates and said two uprights or rods, said wedges having different shapes according to a given angular range to be obtained, a spring fixed to said outer plate and wherein said wedges are provided with at least one groove and a lowered area which accommodates a tooth or teeth of respective tabs located at two ends of the spring, said spring being positioned at the level of a central insert, wherein said wedges, said spring, and said central insert co-operate with the shaped end of said uprights or rods to delimit the angular range of motion of the joint.

2. The joint according to claim 1, in which the spring is fixed to the outer plate by two conical-head rivets holding central insert, the latter acting as a rest for said wedges, as a support for said spring and as a limit stop for the uprights or rods when the wedges are not inserted.

3. The joint according to claim 1, wherein each wedge comprises an additional lowered area forming a pocket to accommodate a gripper for extraction of each wedge, said pocket being present on both sides of the wedge stops.

4. The joint according to claim 1, wherein the side of each wedge presents wording indicating the angular value it must limit in the range of motion (R.O.M.) function.

5. The joint according to claim 1, further comprising a spoked bevel on the wedge stop insertion side, said spoked bevel allowing deformation of said spring and its insertion in said groove.

6. The joint according to claim 1, wherein said spring is first inserted in said grooves and then in the lowered areas of said wedges, whereby said wedges operate by compression, since they are interposed between said uprights or rods to lock them in a predetermined relative angular position.

7. The joint according to claim 1, wherein the shape of said wedges is such that the opposite ends of the uprights or rods touch the wedges simultaneously, thereby preventing any movement and deviation of said wedges.

8. The joint according to claim 1, in which the shaped ends of said uprights or rods encounter said wedges generating a vectorial force which is distributed with horizontal opposed force components that cancel each other out, while the vertical force components hold the wedges in position and are directed towards the central insert, so that the wedges, being inserted between said uprights or rods, cannot slip out, whereby the restraining force of said spring allows just the wedges to be held in position when they are not operating.

9. The joint according to claim 1, further comprising a protective cap acting as an outer cover of the joint, thereby forming an area which ensures that the inserted wedges are held in place, as well as a coupling pin, while the outer side of the cap is provided with toothing for the release of said pin.

10. The joint of claim 9, wherein the inner side of said cap is shaped to allow the positioning and restraint of a gripper for releasing said wedges, said cap being positioned on the outer part of the joint and on the opposite side to a closing cover positioned on the inner side of the joint.

* * * * *